(12) United States Patent
Mukai et al.

(10) Patent No.: US 8,759,030 B2
(45) Date of Patent: Jun. 24, 2014

(54) PROCESS FOR PRODUCING 2-O-ALPHA-D-GLUCOPYRANOSYL-L-ASCORBIC ACID

(75) Inventors: Kazuhisa Mukai, Okayama (JP); Keiji Tsusaki, Okayama (JP); Michio Kubota, Okayama (JP); Shigeharu Fukuda, Okayama (JP); Toshio Miyake, Okayama (JP)

(73) Assignee: Hayashibara Co., Ltd., Okayama-Shi, Okayama (JP)

( * ) Notice: Subject to any disclaimer, the term of this patent is extended or adjusted under 35 U.S.C. 154(b) by 1079 days.

(21) Appl. No.: 10/523,920

(22) PCT Filed: Jul. 7, 2003

(86) PCT No.: PCT/JP03/08600
§ 371 (c)(1),
(2), (4) Date: Feb. 7, 2005

(87) PCT Pub. No.: WO2004/013344
PCT Pub. Date: Feb. 12, 2004

(65) Prior Publication Data
US 2006/0216792 A1    Sep. 28, 2006

(30) Foreign Application Priority Data
Aug. 6, 2002    (JP) .................................. 2002-228705

(51) Int. Cl.
*C12P 19/44*    (2006.01)

(52) U.S. Cl.
USPC .................. 435/74; 435/41; 435/72; 514/474; 549/315

(58) Field of Classification Search
None
See application file for complete search history.

(56) References Cited

U.S. PATENT DOCUMENTS 5,137,723 A * 8/1992 Yamamoto et al. ........... 424/400

FOREIGN PATENT DOCUMENTS

| EP | 0 398 484 A2 | 11/1990 |
| EP | 0 425 066 A1 | 5/1991 |
| EP | 0 539 196 A1 | 4/1993 |
| EP | 1 229 112 | 8/2002 |
| WO | 01/90338 A1 | 11/2001 |

OTHER PUBLICATIONS

BeMiller JN et al. 1996. "Carbohydrates." In Fennema OR, ed. "Food Chemistry, 3rd ed." (CRC Press). pp. 199-200.*
Dokic P et al. 1998. Molecular characteristics of maltodextrins and rheological behavior of diluted and concentrated solutions. Coll Surf A 141: 435-440.*
Wang Y-J et al. 2000. Structures and properties of commercial maltodextrins from corn, potato, and rice starches. Starch 52: 296-304.*
Tanaka, M., et al, "Characterization of *Bacillus stearithermophilus* cyclodextrin glucanotransferase in ascorbic acid 2-O-α-glucoside formation", Biochimica et Biophysica Acta. (1991) 1078:127-132.
Nishimoto, Tomoyuki et al., "Purification and Characterization of Glucosyltransferase and Glucanotransferase involved in the production of Cyclic tetrasaccharide in *Bacillus globisporus* C11", Bioscience Biotechnology Biochemistry, Japan Society for Bioscience, Biotechnology, and Agrochemistry, Tokyo, Japan, vol. 66, No. 9, Sep. 1, 2002, pp. 1806-1818, XP002428055.

* cited by examiner

*Primary Examiner* — Lora E Barnhart Driscoll
(74) *Attorney, Agent, or Firm* — Browdy and Neimark, PLLC

(57) ABSTRACT

The object of the present invention is to provide a method and a process for producing 2-O-α-glucopyranosyl-L-ascorbic acid where 5-O-α-glucopyranosyl-L-ascorbic acid and 6-O-α-glucopyranosyl-L-ascorbic acid are not formed or formed in such a small amount that the formation of these can nor be detected. The present invention solves the above object by providing a process for producing 2-O-α-glucopyranosyl-L-ascorbic acid comprising the steps of allowing α-isomaltosyl glucosaccharide-forming enzyme together with or without cyclomaltodextrin glucanotransferase (EC 2.4.1.19) to act on a solution comprising L-ascorbic acid and, an α-glucosyl saccharide to form 2-O-α-glucopyranosyl-L-ascorbic acid and collecting the formed 2-O-α-glucopyranosyl-L-ascorbic acid.

7 Claims, 1 Drawing Sheet

PROCESS FOR PRODUCING 2-O-ALPHA-D-GLUCOPYRANOSYL-L-ASCORBIC ACID

TECHNICAL FIELD

The present invention relates to a process for producing 2-O-α-D-glucopyranosyl-L-ascorbic acid (abbreviated as "AA-2G", hereinafter), particularly, a process for producing AA-2G, comprising the steps of transferring a glucosyl residue from an α-glucosyl saccharide to L-ascorbic acid using an α-isomaltosyl glucosaccharide-forming enzyme together with or without cyclomaltodextrin glucanotransferase, and collecting the resulting AA-2G from the reaction mixture which contains transferred products.

BACKGROUND ART

As disclosed in Japanese Patent Kokai Nos. 135,992/91 and 139,288/91, AA-2G is a type of saccharide derivative of L-ascorbic acid with a chemical structure represented by Chemical formula 1, which has a satisfactorily high stability but no reducing power. Further, AA-2G is easily hydrolyzed in living bodies to exhibit biological activities inherent to L-ascorbic acid.

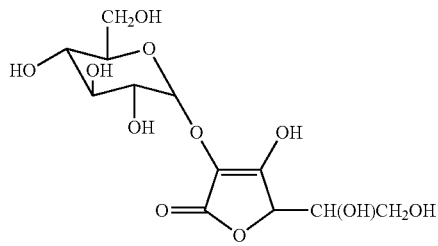

Chemical formula 1

Japanese Patent Kokai No. 183,492/91 discloses a process for producing AA-2G, which maybe carried out in an industrial scale. The process comprises the steps of:

allowing a saccharide-transferring enzyme with or without glucoamylase (EC 3.2.1.3) to act on a solution containing as substrates L-ascorbic acid and an α-glucosyl saccharide to form AA-2G and by-products;

subjecting the resulting reaction mixture containing AA-2G together with other by-products and remaining substrates to a column chromatography using a strongly-acidic cation exchange resin to collect from the eluate one or more fractions which are rich in a high AA-2G;

concentrating the obtained fraction(s) into a supersaturated solution; and crystallizing and collecting AA-2G in the solution.

However, it is known that in the case of using cyclomaltodextrin glucanotransferase (EC 2.4.1.19) (abbreviated as "CGTase", hereinafter) as the saccharide-transferring enzyme, 5-O-α-glucopyranosyl-L-ascorbic acid as represented by Chemical formula 2 (abbreviated as "AA-5G", hereinafter,) and 6-O-α-glucopyranosyl-L-ascorbic acid as represented by Chemical formula 3 (abbreviated as "AA-6G", hereinafter), both of which are structural isomers of AA-2G, are inevitably formed as by-products together with AA-2G. Also, it is known that in the case of using α-glucosidase as the saccharide-transferring enzyme, AA-6G is formed as a by-product together with AA-2G. L-Ascorbic acid and glucose, which are present with AA-2G in reaction mixtures, can be easily separated from AA-2G by a column chromatography using a strongly-acidic cation exchange resin because AA-2G is distinct from L-ascorbic acid and glucose with respect to with their molecular weight. However, AA-5G and AA-6G, formed as by-products along with AA-2G, are hardly separated from AA-2G because they have the same molecular weight. Thus, the presence of AA-5G and AA-6G may prevents the purification of AA-2G, as well as inhibit the subsequent crystallization of AA-2G in supersaturated solutions.

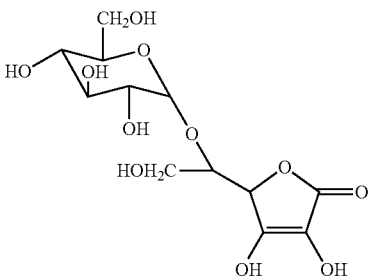

Chemical formula 2

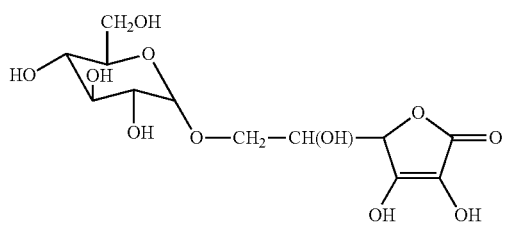

Chemical formula 3

Furthermore, when crystalline AA-2G is collected from the first massecuite and the remaining mother liquor is then subjected to the second and third crystallization steps, AA-5G and AA-6G (isomers of AA-2G) in the mother liquor may inhibit the crystallization of AA-2G to reduce its yield of the second and the third crystallization steps.

As disclosed in Japanese Patent Kokai No. 117,290/93, AA-5G and AA-6G can be eliminated by advantageously utilizing their oxidizabilities which originate from their reducing powers. Particularly, a high AA-2G content product can be produced through the steps of oxidizing such an isomer with a reducing power where reaction mixtures containing the isomer and AA-2G are subjected to an effective oxidizing treatment; and separating AA-2G from the mixtures which contain AA-2G together with the resulting oxidized derivatives of AA-5G and AA-6G.

However, in order to subject a reaction mixture containing AA-2G and isomers with a reducing power to an oxidizing treatment and to attain a prescribed oxidization, it is necessary to chose conditions for oxidization which do oxidize the isomers while leaving AA-2G intact; For example, one can employ a method where the reaction mixture is exposed to aerobic conditions by aeration and agitation. Such a treatment inevitably requires complicated handling and controls; for example, consistently keeping the reaction mixture at a slightly acidic or alkaline pH level; admixing an oxidation-promoting agent such as metal salts including copper salts, iron salts, and the like, active charcoals such as steamed charcoal and zinc chloride charcoal with the reaction mixture; or admixing an oxidizing agent such as hydrogen peroxide, potassium permanganate, etc. with the reaction mixture. If oxidizing treatment is insufficient, isomers with reducing power still remain in the reaction mixture. On the contrary, if oxidation is excessive, AA-2G is affected, resulting in a reduced yield for AA-2G rich products. Oxidation treatment is usually required him or her to accurate control of the reaction condition to keep progress of oxidization at a prescribed level. Because of these, the above described treatments become very costly.

The present invention is established to solve the disadvantage of the conventional process for producing AA-2G described above. The present invention provides a process for producing AA-2G, not requiring the separation of the structural isomers and enabling the efficient production of AA-2G.

DISCLOSURE OF INVENTION

The inventors of the present invention considered that a high AA-2G content product with a high purity can be produced in an industrial scale and a high yield without applying a step of removing AA-5G and AA-6G, glucosyl derivatives of L-ascorbic acid with a reducing power, by oxidizing, if it is possible that a solution, containing AA-2G but not containing AA-5G and AA-6G, can be produced by the initial steps of allowing a saccharide-transferring enzyme to act on a solution containing L-ascorbic acid and α-glucosyl saccharide; and successively allowing glucoamylase to act on the resulting reaction mixture in the process of producing AA-2G. Therefore, the present inventors have extensively studied to establish the method of forming AA-2G without forming AA-5G and AA-6G.

As a result, the inventors of the present invention unexpectedly found that AA-2G was formed in a remarkable amount by allowing α-isomaltosyl glucosaccharide-forming enzyme, disclosed in the specification of International Patent Application No. WO 02/10,361, to act on a solution containing L-ascorbic acid and α-glucosyl saccharide; and AA-5G and AA-6G were not formed or formed in such amount that they can not be detected.

It was also revealed that the content of AA-2G in the reaction mixture is increased by using α-isomaltosyl glucosaccharide-forming enzyme together with CGTase for the transglycosylation and successively treating the resulting reaction mixture with glucoamylase, in comparison with the case of using α-isomaltosyl glucosaccharide-forming enzyme alone. Further, it was revealed that structural isomers of AA-2G such as AA-5G and AA-6G were not formed or formed in such amount that they can not be detected in the reaction mixture as in the case of using α-isomaltosyl glucosaccharide-forming enzyme alone for the transglycosylation.

Since the transglucosylation products comprising AA-2G, obtained by the above glucosy-transferring reaction, does not comprise or comprises structural isomers of AA-2G (AA-5G and AA-6G), which are hardly separated from AA-2G by a column chromatography using a strongly-acidic cation exchange resin, in such amount that they can not be detected, the objective AA-2G can be easily purified in a high yield by the chromatography, and a high AA-2G content product with a high purity can be produced in an industrial scale and a high yield.

Also, it was revealed that the process of the present invention is advantageously used for producing crystalline AA-2G in an industrial scale because AA-2G can be easily crystallized in a high yield using a supersaturated solution of the high AA-2G content product with a high purity.

The word "not formed or formed in such amount that they can not be detected" means the content of a substance of less than 0.1% (w/w) (throughout the specification, "% (w/w)" is abbreviated as "%" hereinafter, unless specified otherwise), on a dry solid basis, of reaction mixture. The word "having a reducing power" means that the substance reduces and decolors 2,6-dichlorophenol-indophenol as in the case of L-ascorbic acid.

The word "L-ascorbic acid" as referred to as in the present invention means L-ascorbic acid including free L-ascorbic acid, salts of L-ascorbic acid such as alkaline metal salts and alkaline earth metal salts, and their mixtures.

Similarly, the words, "AA-2G", "AA-5G", "AA-6G", and α-glycosyl-L-ascorbic acid mean those in free- and salt-forms.

The followings concretely explain the method for the transglucosylation using α-isomaltosyl glucosaccharide-forming enzyme together with or without CGTase in the present invention.

BEST MODE FOR CARRYING OUT THE INVENTION

Figure 1:
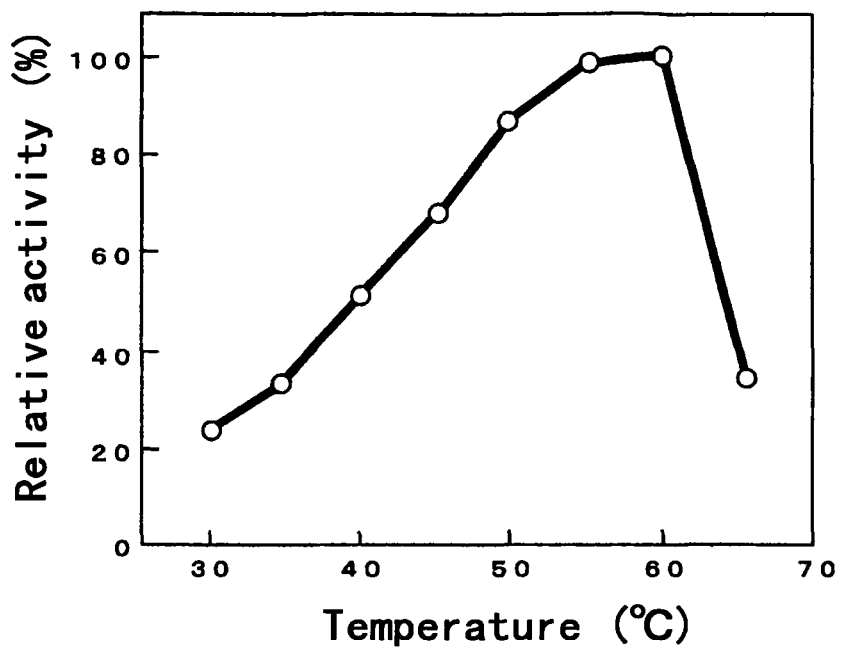
FIG. 1 shows the effects of temperature on AA-2G-forming activity of α-isomaltosyl glucosaccharide-forming enzyme originated from *Arthrobacter globiformis* A19.

α-Glucosyl saccharide as referred to as in the present invention means a saccharide having a α-glucosyl residue. Various α-glucosyl saccharides can be used as far as they can be used for producing AA-2G and/or 2-O-α-glycosyl-L-ascorbic acid (abbreviated as "AA-2Gn", hereinafter) from L-ascorbic acid by the action of α-isomaltosyl glucosaccharide-forming enzyme alone or together with CGTase. For example, maltooligosaccharides such as maltose, maltotriose, maltotetraose, maltopentaose, maltohexaose, maltoheptaose, and maltooctaose; maltodextrin, cyclodextrin, amylose, amylopectin, soluble starch, liquefied starch, gelatinized starch, and glycogen can be arbitrarily used as the α-glucosyl saccharide.

The preferable concentration of L-ascorbic acid in the substrate solution is in the range of, usually, 1% (w/v) or higher, more preferably, about 2 to 30% (w/v). The preferable amount of α-glucosyl saccharide is in the range of, usually, 0.5 to 30 parts by weight to one part by weight of L-ascorbic acid.

As disclosed in the specification of International Patent Application No. WO 02/10,361, α-isomaltosyl glucosaccharide-forming enzyme used in the present invention has an activity of forming a saccharide with a glucose polymerization degree of 3 or higher and bearing both the α-1,6 glucosidic linkage as a linkage at the non-reducing end and the α-1,4 glucosidic linkage other than the linkage at the non-reducing end from a saccharide with a glucose polymerization degree of 2 or higher and bearing the α-1,4 glucosidic linkage as a linkage at the non-reducing end by α-glucosyl-transferring reaction without substantially increasing the reducing power of the reaction mixture. For concrete example, α-isomaltosyl glucosaccharide-forming enzyme, having physicochemical properties described below, can be used in the present invention. One or more saccharides selected from the group consisting of maltooligosaccharides such as maltose, maltotriose, maltotetraose, maltopentaose, maltohexaose, maltoheptaose, and maltooctaose; maltodextrin, cyclodextrin, amylose, amylopectin, soluble starch, liquefied starch, gelatinized starch, and glycogen can be used as aforesaid saccharide with a glucose polymerization degree of 2 or higher and bearing the α-1,4 glucosidic linkage as a linkage at the non-reducing end.

(1) Action

Forming a saccharide with a glucose polymerization degree of 3 or higher and bearing both the α-1,6 glucosidic linkage as a linkage at the non-reducing end and the α-1,4 glucosidic linkage other than the linkage at the non-reducing end from a saccharide with a glucose polymerization degree of 2 or higher and bearing the α-1,4 glucosidic linkage as a linkage at the non-reducing end by α-glucosyl-transferring reaction without substantially increasing the reducing power of the substrate solution;

(2) Molecular Weight

About 74,000 to about 160,000 daltons when determined on SDS-PAGE;

(3) Isoelectric Point (pI)

About 3.8 to 7.8 when determined on isoelectorophoresis using ampholyte;

(4) Optimum Temperature

About 40 to 50° C. when incubated at a pH of 6.0 for 60 min;

About 45 to 55° C. when incubated at a pH of 6.0 for 60 min in the presence of 1 mM $Ca^{2+}$;

About 60° C. when incubated at a pH of 8.4 for 60 min; or

About 65° C. when incubated at a pH of 8.4 for 60 min in the presence of 1 mM $Ca^{2+}$;

(5) Optimum pH

About 6.0 to 8.4 when incubated at 35° C. for 60 min;

(6) Thermal Stability

Stable in the temperature range of about 45° C. or lower when incubated at a pH of 6.0 for 60 min;

Stable in the temperature range at of about 50° C. or lower when incubated at a pH of 6.0 for 60 min in the presence of 1 mM $Ca^{2+}$;

Stable in the temperature range of about 55° C. or lower when incubated at a pH of 8.0 for 60 min; or Stable in the temperature range of about 60° C. or lower when incubated at a pH of 8.0 for 60 min in the presence of 1 mM $Ca^{2+}$;

(7) pH Stability

Stable in a pH range of about 4.5 to 10.0 when incubated at 4° C. for 24 hours; and (8) N-Terminal Amino Acid Sequence Having an N-terminal amino acid sequence of:

```
                                          (SEQ ID NO: 1)
Tyr-Val-Ser-Ser-Leu-Gly-Asn-Leu-Ile,
                                          (SEQ ID NO: 2)
His-Val-Ser-Ala-Leu-Gly-Asn-Leu-Leu,
or
                                          (SEQ ID NO: 3)
Ala-Pro-Leu-Gly-Val-Gln-Arg-Ala-Gln-Phe-Gln-Ser-Gly
```

α-Isomaltosyl glucosaccharide-forming enzyme usable in the present invention transfers a glucosyl residue to L-ascorbic acid to form AA-2G and AA-Gn produced by transferring one or more α-glucopyranosyl-residues to AA-2G when a saccharide with a glucose polymerization degree of 2 or higher, having an α-1,4 glucosidic linkage as a linkage of non-reducing end, was used as a glucosyl donor.

α-Isomaltosyl glucosaccharide-forming enzyme derived from a microorganism selected from the genera *Arthrobacter* and *Bacillus* can be used in the present invention. For example, the enzymes derived from *Arthrobacter globiformis* A19 (FERM BP-7590), *Bacillus globisporus* C9 (FERM BP-7143), *Bacillus globisporus* C11 (FERM BP-7144), and *Bacillus globisporus* N75 (FERM BP-7590) can be arbitrarily used. Also, the enzymes, derived from mutants of those such as a α-isomaltosyl glucosaccharide-forming enzyme-hyper-producing strain obtainable by inducing artificial mutation into such microorganism by using mutation-inducing chemicals such as NTG; irradiating ultraviolet-ray or other rays; or screening naturally-occurring mutant; can be advantageously used. Furthermore, the enzymes derived from self-cloned microorganisms or recombinants; constructed by introducing a intact DNA encoding the polypeptide of α-isomaltosyl glucosaccharide-forming enzyme; or a mutated DNA formed by replacing, deleting, or adding one or more base; into the same or different kind of cell after chemically synthesizing the DNA or cloning the DNA form a cell; can be used.

CGTase usable in the present invention can be arbitrarily selected from those derived from a microorganism selected from the genera of *Bacillus, Klebsiella, Thermoanaerobacter, Brevibacterium, Thermococcus*, etc. As in the case of α-isomaltosyl glucosaccharide-forming enzyme, CGTases derived from self-cloned microorganisms or recombinants; constructed by introducing a intact DNA encoding the polypeptide of CGTase; or a mutated DNA formed by replacing, deleting, or adding one or more base; into the same or different kind of cell after chemically synthesizing the DNA or cloning the DNA form a cell; can be used.

It is not necessary to use those saccharide transferring enzymes in a purified form. Usually, the object of the present invention can be achieved by using crude enzymes. Optionally, the enzymes can be used after purifying with conventional various techniques.

The amount of enzyme and reaction time were closely related to each other. Usually, the amount of enzyme was selected to complete the reaction in about three to 80 hours from the viewpoint of the cost.

In the case of using α-isomaltosyl glucosaccharide-forming enzyme together with CGTase, the contents of AA-5G and AA-6G, both of which are by-products of CGTase reaction, remarkably increased when used CGTase in an excess amount and the formation of the by-products affects on the effect of the present invention. Therefore, the amount of CGTase used in the present invention is preferably selected from the range of about 0.01 to 50 units/g-α-glucosyl saccharide as substrate. The activity of CGTase is assayed by admixing CGTase with 0.3% starch solution containing 20 mM sodium acetate buffer (pH 5.5) and 2 mM calcium chloride and incubating at 40° C. for 10 min. One unit of the activity is defined as the amount of enzyme that decreasing the color of iodine corresponding to 15 mg of the starch in the substrate solution.

α-Isomaltosyl glucosaccharide-forming enzyme and CGTase can be immobilized on gels separately or on the same gel. The immobilized saccharide-transferring enzyme(s) can be advantageously used for the reaction by the mode of batch-repeating reaction or continuous reaction.

Usually, the method for transferring a glucosyl residue in the present invention can be carried out by adding α-isomaltosyl glucosaccharide-forming enzyme together with or without CGTase to aforesaid solution containing L-ascorbic acid and α-glucosyl saccharide under the condition that the enzyme(s) can act sufficiently, desirably, the condition selected from the pH range of about 3 to 10, and the temperature range of 30 to 70° C.

Since L-ascorbic acid is easily decomposed by the oxidation during the reaction, it is desirable to keep the reaction mixture under anaerobic or reduced and shaded condition. If necessary, the reaction can be advantageously carried out in the presence of thiourea, hydrogen sulfide, and the like. In the case of using α-isomaltosyl glucosaccharide-forming enzyme alone or together with CGTase for transferring a glucosyl residue to L-ascorbic acid, 2-O-α-glycosyl-L-ascorbic acid (AA-2Gn), substance where one or more glucopyranosyl residues are bound to AA-2G, is also formed as well as AA-2G in the reaction mixture.

However, by using α-isomaltosyl glucosaccharide-forming enzyme alone or together with CGTase, by-products such as AA-5G and AA-6G, which are hardly separated from AA-2G by an industrial-scale column chromatography, are not formed or formed in such amount that they can not be detected.

The reaction products, obtained by the action of α-isomaltosyl glucosaccharide-forming enzyme alone or together with CGTase, comprise AA-2Gn, derivatives of AA-2G having higher molecular weights than AA-2G. Sine glucoamylase hydrolyzes α-1,4 and α-1,6 glucosidic linkages in the glycosyl moiety of AA-2Gn, AA-2Gn can be converted into AA-2G by allowing glucoamylase to act on the reaction products.

The conditions of the above glucoamylase treatment such as reaction pH, reaction temperature, the amount of glucoamylase, reaction time, and the like can be arbitrarily selected as far as AA-2G can be formed by hydrolyzing AA-2Gn. Immobilized glucoamylases, prepared by support-binding method, crosslinking method, or entrapping method, can be advantageously used for the glucoamylase treatment. Both continuous and batch reaction system can be used for the treatment. Immobilized glucoamylase can be separated from the reaction mixture by the technique such as filtration by membrane, and advantageously used again for the reaction.

After the completion of the reaction, the reaction mixture is usually heated to inactivate enzymes, decolored with activated charcoal, filtrated to remove impurities, and, optionally, concentrated. The resulting solution contains the objective AA-2G; and remaining L-ascorbic acid and neutral saccharides including D-glucose as other components. The contents of neutral saccharides including glucose can be decreased by separating the neutral saccharides and AA-2G by electrodialysis method or a column chromatography using an anion-exchange resin; and removing the resulting fractions containing the neutral saccharide. A high AA-2G content fractions can be obtained by subjecting the above solution containing AA-2G to a column chromatography using a strongly-acidic cation exchange resin.

Conventional strongly-acidic cation exchange resins can be arbitrarily used in the present invention. For example, styrene-divinylbenzene macroreticular resins, having sulfonyl residues, in the form of alkaline-metal salts such as $Na^+$-form, $K^+$-form, and the like, alkaline-earth metal salts such as $Ca^{++}$-form, and $Mg^{++}$-form, and the like, and $H^+$-form, can be used. For example, "DOWEX® 50WX8", a resin commercialized by The Dow Chemical Company, Indiana, USA; "AMBERLITE® CG-6000" and "XT-1022E", resins commercialized by Rohm and Hass Company, Philadelphia, USA; and "DIAION® SK104", a resin commercialized by Mitsubishi Chemical Industries, Ltd., Tokyo, Japan, can be used as commercially available strongly-acidic cation exchange resins.

In the case of using a solution containing the objective AA-2G and other components including L-ascorbic acid and D-glucose as a material solution, a high AA-2G content product can be easily produced by the steps of:

subjecting the material solution to a column packed with a strongly-acidic cation exchange resin;

separating the material into Fraction A containing AA-2G in a high content, Fraction B containing AA-2G, L-ascorbic acid, and D-glucose, and Fraction C containing L-ascorbic acid and D-glucose, in that order by eluting with water; and collecting the resulting high AA-2G content fractions.

Further, in the fractionation of the material solution, the high AA-2G content product can be advantageously obtained in a high concentration and a high yield using a relatively small amount of water by subjecting the above obtained Fraction B before and after subjecting the material solution. The method for the fractionation can be arbitrarily selected from fixed-bed method, moving-bed method, and semi-moving bed method.

The high AA-2G content product, desirably, in a content of 70% or higher, is stable even in the form of solution or concentrated syrup, and can be easily used. Usually, crystalline AA-2G is produced by concentrating the high AA-2G content product into a supersaturated solution and crystallizing AA-2G. Since structural isomers of AA-2G, having a reducing power and inhibiting the crystallization of AA-2G, are not substantially comprised in the reaction mixture at the initial stage of saccharide-transferring reaction, AA-2G in the high AA-2G content product for crystallization of the present invention is easily crystallized in a high yield. Usually, the massecuite containing crystalline AA-2G can be obtained by placing supersaturated AA-2G solution at a temperature of 20 to 60° C. into a crystallizer, admixing 0.1 to 2% of seed crystal, and stirring gently and cooling gradually to promote the crystallization.

As described above, crystalline AA-2G can be easily produced by admixing seed crystal with the supersaturated solution of AA-2G.

To collect crystalline AA-2G from the resulting massecuite, centrifugal separation method, block-pulverizing method, fluidized granulation method, spray-drying method, and the like can be arbitrarily used.

Crystalline AA-2G, obtainable by the above procedures, is substantially non- or hardly-hygroscopic. The powdery crystalline AA-2G shows a satisfactory fluidity and can be used regardless of solidification. Advantageous properties of crystalline AA-2G are as follows:

(1) AA-2G shows no reducing power and is extremely stable. Different from the case of L-ascorbic acid, AA-2G hardly causes Maillard reaction. Therefore, AA-2G does not react with amino acids, peptides, proteins, lipids, saccharides, biologically active substances, and the like and is able to stabilize those.

(2) AA-2G is hydrolyzed into L-ascorbic acid and D-glucose, and exhibits reducing power and anti-oxidizing activities of L-ascorbic acid.

(3) AA-2G is easily hydrolyzed into L-ascorbic acid and D-glucose by an enzyme in living bodies and exhibits biological activities inherent to L-ascorbic acid. Also, by using AA-2G together with vitamins E and P, those biological activities can be increased.

(4) It is possible that AA-2G is produced and metabolized in living bodies when L-ascorbic acid and α-glucosyl saccharide are orally in taken. Therefore, AA-2G is recognized as a highly safe substance.

(5) Although crystalline AA-2G is substantially non- or hardly-hygroscopic, AA-2G is easily dissolved in water and shows a high solubility. AA-2G can be advantageously used as vitamin C-reinforcement, taste-improving agent, acidifier, stabilizer, and the like for vitamin in the form of powder, granule, tablet, and the like, or foods such as cream, chocolate, chewing gum, instant juice, instant seasoning, and the like.

(6) Crystalline AA-2G is substantially non- or hardly hygroscopic. Since the powder of crystalline AA-2G shows no-solidification and a satisfactory fluidity, it can be used easily. Therefore, by using the powdery crystalline AA-2G, physical and personnel costs for packing, transporting, and preserving can be vastly reduced.

The following experiments concretely explain the method for transferring a saccharide to L-ascorbic acid of the present invention.

Experiment 1

Preparation of α-Isomaltosyl Glucosaccharide-Forming Enzyme

A liquid culture medium consisting 4% (w/v) of "PINE-DEX #4", a partial starch hydrolyzate, 1.8% (w/v) of "ASA-HIMEAST", a yeast extract, 0.1% (w/v) of dipotassium phosphate, 0.06% (w/v) of sodium phosphate dodeca-hydrate, 0.05% (w/v) of magnesium sulfate hepta-hydrate, and water was placed in 500-ml Erlenmeyer flasks in a respective amount of 100 ml, sterilized by autoclaving at 121° C. for 20 minutes, cooled and seeded with *Arthrobacter globiformis* A19 (FERM BP-7590), followed by culturing under rotary-shaking conditions at 27° C. and 230 rpm for 48 hours for a seed culture. About 20 of a fresh preparation of the same liquid culture medium as used in the above seed culture were placed in a 30 L fermentor, sterilized by heating, and then cooled to 27° C. and inoculated with 1% (v/v) of the seed culture, followed by culturing at 27° C. and pH 6.0 to 9.0 for 48 hours under aeration-agitation conditions. After the completion of the culture, about 1.1 unit/ml of α-isomaltosyl glucosaccharide-forming enzyme activity was detected in the resulting culture by measuring the enzyme activity. About 18 L of supernatant obtained by centrifugation (10,000 rpm, 30 minutes) had about 1.06 units/ml of α-isomaltosyl glucosaccharide-forming enzyme activity, i.e., a total activity of about 19,100 units.

The activity of α-isomaltosyl glucosaccharide-forming enzyme was measured by the following assay: A substrate solution was prepared by dissolving maltotriose in 100 mM Glycine-NaOH buffer (pH 8.4) to give a concentration of 2% (w/v). A reaction mixture was prepared by mixing 0.5 ml of the substrate solution and 0.5 ml of an enzyme solution, and incubated at 40° C. for 60 minutes. After stopping the reaction by boiling for 10 minutes, the amount of maltose formed in the reaction mixture was determined by high-performance liquid chromatography (HPLC). One unit of α-isomaltosyl glucosaccharide-forming activity was defined as the amount of the enzyme that forms one μmole of maltose per minute under the above conditions. HPLC was carried out using "SHODEX KS-801", a column commercialized by Showa Denko K.K., Tokyo, Japan, at a column temperature of 60° C. and a flow rate of 0.5 ml/minutes of water, and using "RI-8012", a differential refractometer commercialized by Tosoh Corporation, Tokyo, Japan.

Experiment 2

Purification of α-Isomaltosyl Glucosaccharide-Forming Enzyme

About 18 L of the culture supernatant obtained by the method described in Experiment 1 was salted out with 80% saturated ammonium sulfate solution and allowed to stand at 4° C. for 24 hours, and the formed precipitates were collected by centrifugation (10,000 rpm, 30 minutes), dissolved in 10 mM Tris-HCl buffer (pH 7.5), and dialyzed against the same buffer to obtain about 850 ml of a crude enzyme solution. The crude enzyme solution had about 8,210 units of α-isomaltosyl glucosaccharide-forming enzyme. The crude enzyme solution was subjected to an ion-exchange column chromatography using 380 ml of "DEAE-TOYOPEARL 650S" gel commercialized by Tosoh Corporation, Tokyo, Japan. The active component was adsorbed on "DEAE-TOYOPEARL 650S" gel and, then sequentially eluted with a linear gradient increasing from 0 M to 1 M of sodium chloride. α-Isomaltosyl glucosaccharide-forming enzyme was eluted with a linear gradient of sodium chloride at about 0.2 M. Thus, fractions with the α-isomaltosyl glucosaccharide-forming enzyme activity were collected as partially purified preparation of α-isomaltosyl glucosaccharide-forming enzyme.

The partially purified enzyme preparation having α-isomaltosyl glucosaccharide-forming activity, thus obtained, was dialyzed against 10 mM sodium phosphate buffer (pH 7.0) with 1 M ammonium sulfate. The dialyzed solution was centrifuged to remove impurities, and subjected to an affinity column chromatography using 500 ml of "SEPHACRYL HR S-200", a gel commercialized by Amersham Biosciences K. K., Tokyo, Japan. The enzyme was adsorbed on "SEPHACRYL HR S-200" gel and, when eluted with a linear gradient decreasing from 1 M to 0 M of ammonium sulfate, the enzymatic activity was eluted with a linear gradient of ammonium sulfate at about 0.2 M, and fractions with the enzyme activity was collected as purified enzyme preparation.

TABLE 1

| Enzyme | Amount of Enzyme (units/g-sub.) | Content (%) | | |
|---|---|---|---|---|
| | | AA-2G | AA-5G | AA-6G |
| IMG* from *Arthrobacter* sp. | 5 | 22.5 | 0.0 | 0.0 |
| | 10 | 24.0 | 0.0 | 0.0 |
| | 20 | 24.3 | 0.0 | 0.0 |
| CGTase** (Control) | 300 | 25.5 | 0.8 | 0.3 |

*IMG; α-isomaltosyl glucosaccharide-forming enzyme
**CGTase; cyclomaltodextrin glucanotransferase The finally purified α-isomaltosyl glucosaccharide-forming enzyme preparation was assayed for purity on gel electrophoresis using a 7.5% (w/v) polyacrylamide gel and detected on the gel as single protein band, i.e., a high purity enzyme.

Experiment 3

Properties of α-Isomaltosyl Glucosaccharide-Forming Enzyme

Experiment 3-1

Molecular Weight

A purified preparation of α-isomaltosyl glucosaccharide-forming enzyme, obtained by the method in Experiment 2, was subjected to SDS-PAGE using 7.5% (w/v) of polyacrylamide gel and then determined for its molecular weights by comparing with the dynamics of standard molecular weight markers electrophoresed in parallel, commercialized by Bio-Rad Laboratories, Inc., Brussels, Belgium. It was revealed that the enzyme had molecular weights of about 94,000± 20,000 daltons.

Experiment 3-2

Isoelectric Point

A purified preparation of the α-isomaltosyl glucosaccharide-forming enzyme, obtained by the method in Experiment 2, was subjected to isoelectrophoresis using a gel containing 2% (w/v) "AMPHOLINE®", a carrier ampholyte commercialized by Amersham Biosciences K.K., Tokyo, Japan, and then measured pHs of protein band and gel to determine their isoelectric points. It was revealed that the enzyme had isoelectric point of about 4.3±0.5.

Experiment 3-3

Optimum Temperature and Optimum pH

The effect of temperature and pH on the α-isomaltosyl glucosaccharide-forming enzyme activity was examined in accordance with the assay for the α-isomaltosyl glucosaccharide-forming enzyme activity, described in Experiment 1, under various temperature and pH conditions. The optimum temperature of the enzyme was about 60° C. (in the absence of $Ca^{2+}$) and about 65° C. (in the presence of 1 mM $Ca^{2+}$) when incubated at pH 8.4 for 60 min, and the optimum pH was about 8.4 when incubated at 35° C. for 60 minutes.

Experiment 3-4

Stability

The thermal stability of α-isomaltosyl glucosaccharide-forming enzyme was determined by incubating the testing enzyme solution in 20 mM Glycine-NaOH buffer, pH 8.0 at prescribed temperatures for 60 minutes in the presence or absence of 1 mM $Ca^{2+}$, cooling with water the resulting polypeptide solutions, and assaying the residual enzyme activity of each solution. The pH stability of α-isomaltosyl glucosaccharide-forming enzyme was determined by keeping the testing enzyme solutions in 50 mM buffer having prescribed pHs at 4° C. for 24 hours, adjusting the pH of each solution to 8.0, and assaying the residual enzyme activity of each solution. The thermal stability of the enzyme was up to about 55° C. (in the absence of $Ca^{2+}$) and about 60° C. (in the presence of 1 mM $Ca^{2+}$), and pH stability of about 5.0 to about 9.0.

Experiment 3-5

N-Terminal Amino Acid Sequence

A purified preparation of α-isomaltosyl glucosaccharide-forming enzyme was subjected to N-terminal sequence analysis by using "Protein sequencer model 473A", an apparatus of Applied Biosystems, Foster City, USA. It was revealed that α-isomaltosyl glucosaccharide-forming enzyme had an amino acid sequence of SEQ ID NO: 3.

Although the purification and properties of α-isomaltosyl glucosaccharide-forming enzyme from *Arthrobacter globiformis* A19 were described above, the enzyme from other strains can be also used in the present invention.

Experiment 4

Glucosyl-Transferring Reaction to L-Ascorbic Acid from Various Glucosyl Saccharides as Glucosyl Donors A test for investigating whether the following each saccharide can be used or not as a glucosyl donor for transferring glucosyl residue to L-ascorbic acid by α-isomaltosyl glucosaccharide-forming enzyme was carried out. A solution containing glucose, maltose, maltotriose, maltotetraose, maltopentaose, maltohexaose, maltoheptaose, isomaltose, isomaltotriose, isopanose, trehalose, kojibiose, nigerose, neotrehalose, cellobiose, gentiobiose, maltitol, maltotriitol, lactose, sucrose, erlose, selaginose, maltosylglucoside, isomaltosylglucoside, α-cyclodextrin, β-cyclodextrin, γ-cyclodextrin, amylose, amylopectin, glycogen, pullulan, or dextran was prepared. To each solution, L-ascorbic acid was further added and the concentrations of the saccharide and L-ascorbic acid were adjusted to 2% (w/v). To each substrate solution, purified α-isomaltosyl glucosaccharide-forming enzyme preparation, obtained by the method in Experiment 2, was added to give 3 units/g-substrate of the amount of enzyme, and the concentration of the substrate was adjusted to 1.6% (w/v), and followed the enzyme reaction at 40° C., pH 6.0 for 20 hours. The formation of AA-2G in the reaction mixture was detected by thin-layer chromatography (abbreviated as "TLC", hereinafter) using a silica gel plate. A mixture of n-butanol, pyridine, and water (volume ratio of 6:4:1) was used as a solvent for the development. After developing samples once on "KIESELGEL $60F_{254}$", silica gel-aluminum plate (20×20 cm) commercialized by Merck Ltd. Japan, Tokyo, Japan, AA-2G and L-ascorbic acid were detected by irradiating ultraviolet-ray. From the results of TLC analysis, the formation of AA-2G was evaluated.

TABLE 2

| IMG* | CGTase** | Content (%) | | |
|---|---|---|---|---|
| (units/g-sub.) | (units/g-sub.) | AA-2G | AA-5G | AA-6G |
| 10 | 0 | 25.1 | 0.0 | 0.0 |
| 10 | 1 | 29.3 | 0.0 | 0.0 |
| 10 | 2 | 30.1 | 0.0 | 0.0 |
| 10 | 5 | 30.8 | 0.1 | 0.0 |
| 10 | 10 | 30.9 | 0.1 | 0.0 |
| 10 | 100 | 30.6 | 0.8 | 0.3 |
| 0 | 1 | 4.3 | 0.0 | 0.0 |
| 0 | 2 | 5.4 | 0.0 | 0.0 |
| 0 | 5 | 7.8 | 0.2 | 0.0 |
| 0 | 10 | 10.4 | 0.3 | 0.1 |
| 0 | 100 | 29.5 | 0.9 | 0.3 |

*IMG; α-isomaltosyl glucosaccharide-forming enzyme
**CGTase; cyclomaltodextrin glucanotransferase It was revealed that α-isomaltosyl glucosaccharide-forming enzyme formed AA-2G by using saccharides, having a maltose structure at their non-reducing end and the glucose polymerization degree of three or higher as glucosyl donors and transferring a glucosyl residue to L-ascorbic acid. Further, it was also revealed that α-isomaltosyl glucosaccharide-forming enzyme formed AA-2G by using saccharides, having a glucose polymerization degree of two such as maltose, kojibiose, nigerose, neotrehalose, maltotriitol, erlose as glucosyl donors.

Experiment 5

Transglucosylation Products from L-Ascorbic Acid

An aqueous solution containing 5% (w/v) of L-ascorbic acid, 5% (w/v) of maltopentaose, and 1 mM of calcium chloride was adjusted at pH 5.0. To the solution, the purified α-isomaltosyl glucosaccharide-forming enzyme, prepared by the method in Experiment 2, was added to give the amount of enzyme of 10 units/g-maltopentaose, and followed the enzyme reaction at 50° C. for 24 hours. After stopping the reaction by boiling the reaction mixture for 10 minutes, a portion of the reaction mixture was withdrawn, admixed with 40 units/g-maltopentaose of glucoamylase commercialized by Seikagaku Corporation, Tokyo, Japan; incubated at 40° C. for 16 hours, and boiled for 10 minutes to stop the reaction. The transglucosylation product from L-ascorbic acid and remaining L-ascorbic acid were separated and those contents in the reaction mixture were determined by the following high performance liquid chromatography (HPLC). HPLC analysis was carried out under the following conditions:

Column: "WAKOPAK WB-T-330", a column commercialized by Wako Pure Chemical Industries, Ltd., Osaka, Japan;
Column temperature: 25° C.
Solvent: 70 ppm of aqueous nitrate solution
Flow rate: 0.5 ml/min The contents of L-ascorbic acid and the transglucosylation products from L-ascorbic acid, d.s.b., were determined by measuring those absorbance at 238 nm using "UV-8020", a spectrophotometor commercialized by Tosoh Corporation, Tokyo, Japan; and measuring the composition of the reaction mixture including those using "RI-8020", a refractive index detector commercialized by Tosoh Corporation, Tokyo, Japan. The results are in Table 1.

TABLE 1

| Glucoamylase treatment | Content (%) | | |
| --- | --- | --- | --- |
| | AA-2G | AA-2Gn* | L-Ascorbic acid |
| before | 18.7 | 0.4 | 40.3 |
| after | 19.1 | 0.0 | 40.3 |

*AA-2Gn means derivatives of AA-2G, having a structure of binding one or more glucopyranosyl residues to AA-2G.

As is evident from the results in Table 1 AA-2G in a content of about 18.7% and a transglucosylation product not identical with AA-2G in a content of about 0.4% were formed as the transglucosylation products by α-isomaltosyl glucosaccharide-forming enzyme. After the glucoamylase treatment, it was revealed that the transgulcosylation product not identical with AA-2G was disappeared to give AA-2G as a sole transglucosylation product from L-ascorbic acid and the content of AA-2G was increased. Taking account of the action pattern of glucoamylase, it was considered that the transglucosylation product not identical with AA-2G is glycosyl L-ascorbic acid constructed by binding one or more glucopyranosyl-residues with AA-2G; and that the glycosyl-residue constructed by one or more glucopyranosyl residues was hydrolyzed by glucoamylase to convert the glycosyl L-ascorbic acid into AA-2G.

Experiment 6

Effects of Temperature and pH on the Formation of AA-2G

The effects of temperature and pH on the AA-2G-forming activity of α-isomaltosyl glucosaccharide-forming enzyme were examined under various temperature and pH conditions. The AA-2G-forming activity was measured as follows:
(1) Effects of Temperature on the AA-2G-Forming Activity To prepare the substrate solution, L-ascorbic acid, maltopentaose, and calcium chloride were dissolved into 100 mM sodium acetate buffer (pH 5.0) to give final concentrations of 0.5% (w/v), 0.5% (w/v), and 1 mM, respectively. To two milliliters of the substrate solution, 0.2 ml of the enzyme solution was added and incubated at 30 to 65° C. for 30 min for the reaction. After stopping the reaction by boiling the reaction mixture, the amount of AA-2G formed in the reaction mixture was determined by HPLC described in Experiment 5.

(2) Effects of pH on the AA-2G-Forming Activity

To prepare the substrate solution, L-ascorbic acid, maltopentaose, and calcium chloride were dissolved into 100 mM of various buffers to give final concentrations of 0.5% (w/v), 0.5% (w/v), and 1 mM, respectively. Sodium acetate buffer, sodium phosphate buffer, and Tris-HCl buffer were used in the pH ranges of pH 4.1 to 6.4, pH 6.7 to 7.5., and pH 7.6 to 8.5, respectively. To two milliliters of the substrate solution, 0.2 ml of the enzyme solution was added and incubated at 40° C. for 30 min for the reaction. After stopping the reaction by boiling the reaction mixture, the amount of AA-2G formed in the reaction mixture was determined by HPLC. The results were shown in FIG. 1 (Effects of temperature) and FIG. 2 (Effects of pH), respectively.

Figure 2:
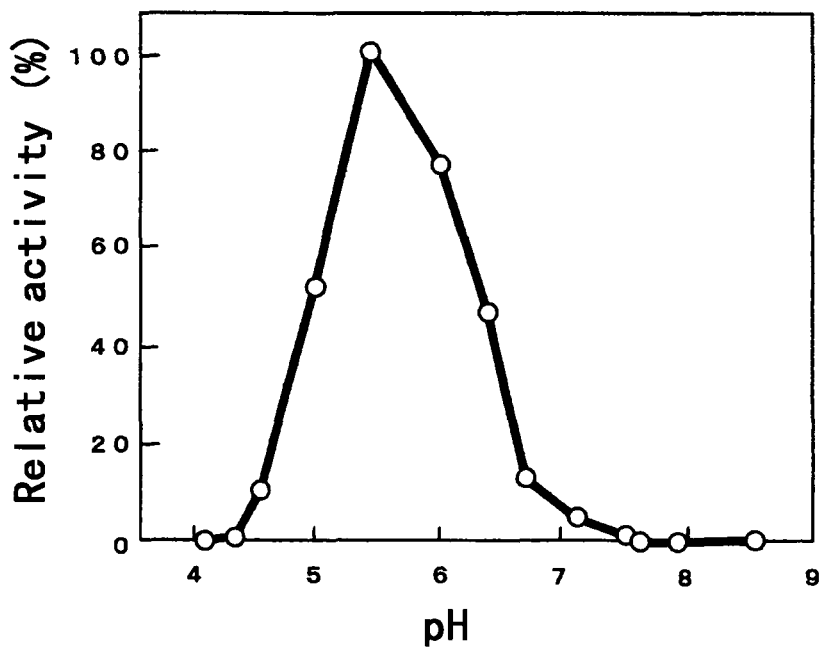
FIG. 2 shows the effects of pH on AA-2G-forming activity of α-isomaltosyl glucosaccharide-forming enzyme originated from *Arthrobacter globiformis* A19.

As is evident from the results in FIG. 1 and FIG. 2, the optimum temperature and optimum pH of the AA-2G-forming activity of α-isomaltosyl glucosaccharide-forming enzyme was about 55 to 60° C. when incubated at pH 5.0 for 30 min and about 5.5 when incubated at 40° C. for 30 min, respectively.

Experiment 7

Formation of AA-2G by α-Isomaltosyl Glucosaccharide-Forming Enzyme

An aqueous substrate solution containing 5% of L-ascorbic acid, 5% of "PINEDEX #1", a partial starch hydrolyzate commercialized by Matsutani Chemical Industry Co., Ltd., Osaka, Japan, and 1 mM calcium chloride was adjusted to pH 5.0. To the substrate solution, the purified α-isomaltosyl glucosaccharide-forming enzyme prepared by the method of Experiment 2 was added to give the amount of enzyme of 5 to 20 units/g-partial starch hydrolyzate, and followed the enzyme reaction at 50° C. for 48 hours. After the completion of the reaction, each reaction mixture was boiled at 100° C. for 10 min to inactivate enzyme, cooled to 40° C., admixed with 40 units/g-partial starch hydrolyzate of glucoamylase commercialized by Seikagaku Corporation, Tokyo, Japan, and followed the enzyme reaction at 40° C. for 16 hours. The contents, d.s.b., of AA-2G, AA-5G, and AA-6G of each reaction mixture were determined by HPLC described in Experiment 5 by using a commercially available AA-2G commercialized by Hayashibara Biochemical Laboratories Inc., Okayama, Japan; and AA-5G and AA-6G, prepared by the method described in the specification of Japanese Patent No. 3,134,235, as standards. Except for using 300 units/g-partial starch hydrolyzate of CGTase commercialized by Hayashibara Biochemical Laboratories Inc., Okayama, Japan, as a substitute of α-isomaltosyl glucosaccharide-forming enzyme, the same reaction was carried out and the contents of AA-2G, AA-5G and AA-6G were determined. The results are in Table 2.

TABLE 2

| Enzyme | Amount of Enzyme (units/g-sub.) | Content (%) | | |
|---|---|---|---|---|
| | | AA-2G | AA-5G | AA-6G |
| IMG* from Arthrobacter sp. | 5 | 22.5 | 0.0 | 0.0 |
| | 10 | 24.0 | 0.0 | 0.0 |
| | 20 | 24.3 | 0.0 | 0.0 |
| CGTase** (Control) | 300 | 25.5 | 0.8 | 0.3 |

*IMG; α-isomaltosyl glucosaccharide-forming enzyme
**CGTase; cyclomaltodextrin glucanotransferase As is evident from the results in Table 2 α-isomaltosyl glucosaccharide-forming enzyme formed AA-2G as a sole transglucosylation product and not formed AA-5G and AA-6G. The control enzyme, CGTase, formed AA-2G in almost same level with the case of α-isomaltosyl glucosaccharide-forming enzyme and also formed AA-5G and AA-6G to give the contents of 0.8% and 0.3%, respectively.

From the above results, it is revealed that α-isomaltosyl glucosaccharide-forming enzyme transfers a glucosyl residue only to 2-hydroxy group of L-ascorbic acid and specifically forms AA-2G while CGTase transfers glucosyl residue not only 2-hydroxyl group of L-ascorbic acid but also 5- and 6-hydroxyl groups and forms AA-2G and by-products, AA-5G and AA-6G.

Experiment 8

Formation of AA-2G by the Combinational Use of α-Isomaltosyl Glucosaccharide-Forming Enzyme and CGTase An aqueous substrate solution of L-ascorbic acid, 21% of "PINEDEX #100", a partial starch hydrolyzate commercialized by Matsutani Chemical Industry Co., Ltd., of Osaka, Japan, and 1 mM calcium chloride was adjusted to pH 5.0. To the substrate solution, 10 units/g-partial starch hydrolyzate of the purified α-isomaltosyl glucosaccharide-forming enzyme prepared by the method of Experiment 2 and 1 to 100 units/g-partial starch hydrolyzate of CGTase were added, and followed the enzyme reaction at 50° C. for 24 hours. After the completion of the reaction, each reaction mixture was boiled at 100° C. for 10 min to inactivate enzyme, cooled to 40° C., admixed with 40 units/g-partial starch hydrolyzate of glucoamylase commercialized by Seikagaku Corporation, Tokyo, Japan, and followed the enzyme reaction at 40° C. for 16 hours. The contents, d.s.b., of AA-2G. AA-5G, and AA-6G of each reaction mixture were determined by HPLC described in Experiment 5. Except for using α-isomaltosyl glucosaccharide-forming enzyme alone or CGTase alone as control tests, the same transferring reaction was carried out and analyzed with the same manner. The results are in Table 5.

TABLE 3

| IMG* (units/g-sub.) | CGTase** (units/g-sub.) | Content (%) | | |
|---|---|---|---|---|
| | | AA-2G | AA-5G | AA-6G |
| 10 | 0 | 25.1 | 0.0 | 0.0 |
| 10 | 1 | 29.3 | 0.0 | 0.0 |
| 10 | 2 | 30.1 | 0.0 | 0.0 |
| 10 | 5 | 30.8 | 0.1 | 0.0 |
| 10 | 10 | 30.9 | 0.1 | 0.0 |
| 10 | 100 | 30.6 | 0.8 | 0.3 |
| 0 | 1 | 4.3 | 0.0 | 0.0 |
| 0 | 2 | 5.4 | 0.0 | 0.0 |
| 0 | 5 | 7.8 | 0.2 | 0.0 |
| 0 | 10 | 10.4 | 0.3 | 0.1 |
| 0 | 100 | 29.5 | 0.9 | 0.3 |

*IMG; α-isomaltosyl glucosaccharide-forming enzyme
**CGTase; cyclomaltodextrin glucanotransferase As is evident from the results in Table 3, in the case of using α-isomaltosyl glucosaccharide-forming enzyme alone, AA-2G was formed in a content of about 25% as a sole transglucosylation product from L-ascorbic acid, and AA-5G and AA-6G were not formed. In the case of using both α-isomaltosyl glucosaccharide-forming enzyme and CGTase, the content of AA-2G was increased to about 29 to 31% and the formation of AA-5G and AA-6G were as follows.

1 to 2 units/g of CGTase; AA-5G and AA-6G were not formed.

5 to 10 units/g of CGTase; AA-5G in the content of about 0.1% was formed.

100 units/g of CGTase; AA-5G and AA-6G was formed in the contents
of about 0.8% and 0.1%, respectively.

In the case of using CGTase alone, AA-5G and AA-6G were not formed in the range of using CGTase of 1 to 2 units/g but the content of AA-2G was low, about 4 to 5%. In the case of using 5 units/g or higher amount of CGTase, the content of AA-2G was increased from about 8% to about 30% with increase of the amount of enzyme but AA-5G and/or AA-6G were formed.

From the above results, it was revealed that the content of AA-2G can be increased by using both α-isomaltosyl glucosaccharide-forming enzyme and CGTase in comparison with the case of using α-isomaltosyl glucosaccharide-forming enzyme alone. Further, it was also revealed that the contents of AA-5G and AA-6G can be decreased to the level that AA-5G and AA-6G were not formed or formed in such a small amount that the formation of these can not be detected; by using a small amount of CGTase together with α-isomaltosyl glucosaccharide-forming enzyme.

The following examples explain the process for producing the high AA-2G content product of the present invention.

Example 1

Nine parts by weight of dextrin (DE of about 6) was dissolved in 28 parts by weight of water by heating. Three parts by weight of L-ascorbic acid was further added to the resulting solution under reducing condition to prepare a substrate solution. The substrate solution was adjusted at pH 5.0 and 40° C., admixed with eight units/g-dextrin of partially purified enzyme preparation having α-isomaltosyl glucosaccharide-forming enzyme activity, prepared by the method in Experiment 2, and followed by the enzymatic reaction for 42 hours. After heating for inactivating enzymes, the reaction mixture was adjusted to 55° C., admixed with 50 units/g-dextrin of glucoamylase, followed by the enzymatic reaction for 16 hours.

After the completion of the reaction, the reaction mixture contained about 24.9%, d.s.b., of AA-2G but AA-5G and AA-6G were not detected. Successively, the reaction mixture was heated to inactivate enzyme, and decolored and filtrated with activated charcoal. The resulting filtrate was passed through a cation exchanger (H⁺ form) column to remove minerals and subjected to an anion exchanger (OH⁻ form) column for allowing anions to adsorb on the exchanger. After washing the anion-exchanger column with water to remove D-glucose and the like, adsorbent was eluted with 0.5 N-hydrochloric acid aqueous solution and the resulting eluate was concentrated.

By HPLC analysis, the resulting concentrate contains about 52.5%, d.s.b., of AA-2G, about 39%, d.s.b., of L-ascorbic acid, and less than about 0.1% of AA-5G and AA-6G. The concentrate was subjected to column chromatography using "AMBERLITE® CG-6000" (H⁺ form), a strongly-acidic cation exchange resin commercialized by Rohm and Hass, Philadelphia, USA, to collect high AA-2G content fractions.

By HPLC analysis, the high AA-2G content fraction contains about 93.6%, d.s.b., of AA-2G, and less than about 0.1% of AA-5G and AA-6G. The fraction was concentrated under reduced pressure to give a concentration of about 77%, placed in a crystallizer, admixed with 2% to total solid basis of crystalline AA-2G as seed crystal, and adjusted to 40° C. The resulting solution was gradually cooled to 20° C. with stirring and taking two days to obtain a massecuite. Crystalline AA-2G was obtained in a yield of about 46%, on the material L-ascorbic acid basis, by centrifuging the massecuite using a basket-type centrifugal separator. Further, mother liquor containing about 82.3%, d.s.b., of AA-2G was collected in a yield of about 28%, on the material L-ascorbic acid basis.

The crystalline AA-2G product shows no reducing power and has sufficient stability and biological activity. Therefore, the product can be advantageously used for foods, anti-susceptive disease agents, cosmetics, and the like as taste-improving agent, acidifier, stabilizer, quality-improving agent, anti-oxidant substance, physiologically active substance, UV-adsorbent, material for pharmaceuticals, and chemicals as well as vitamin C reinforcement.

Example 2

The mother liquor, collected by the method of Example 1, was concentrated, and subjected to a column chromatography using a strongly-acidic cation exchanger, according to the method in Example 2, to collect high AA-2G content fractions. The resulting high AA-2G content fraction contained about 93.0%, d.s.b., of AA-2G and less than 0.1% of AA-5G and AA-6G.

According to the method in Example 1, crystalline AA-2G was obtained in a yield of about 63%, on a dry basis of mother liquor, by concentrating the fraction, crystallizing AA-2G in the resulting concentrate, and separating crystal from the resulting massecuite.

The crystalline AA-2G can be advantageously used for foods, anti-susceptive disease agents, cosmetics, and the like as in the case of Example 1.

Example 3

A mutant strain, producing α-isomaltosyl glucosaccharide-forming enzyme in a high level but not producing α-isomaltosyl-transferring enzyme, was obtained by mutating *Arthrobacter globiformis* A19 (FERM BP-7590) by the conventional mutation using N-methyl-N-nitro-N-nitrosoguanidine as a mutating agent. According to the method described in Experiment 1, the mutant, thus obtained, was cultivated in a liquid culture medium consisting 4% (w/v) of "PINEDEX #4", a partial starch hydrolyzate, 1.8% (w/v) of "ASAHIME-AST", a yeast extract, 0.1% (w/v) of dipotassium phosphate, 0.06% (w/v) of sodium phosphate dodeca-hydrate, 0.05% (w/v) of magnesium sulfate hepta-hydrate, and water, for 72 hours under aeration-agitation conditions. After the completion of the culture, about 14 units/ml-culture of α-isomaltosyl glucosaccharide-forming enzyme activity was detected by the assay of the activity in the resulting culture broth while α-isomaltosyl-transferring enzyme activity was not detected. According to the conventional method, a concentrated enzyme preparation having the α-isomaltosyl glucosaccharide-forming enzyme activity was obtained by removing cells using SF-membrane and concentrating using UF-membrane. About 350 units/ml of the α-isomaltosyl glucosaccharide-forming enzyme activity was detected by the assay of the resulting concentrated enzyme solution.

A corn starch was prepared into about 20% starch suspension, admixed with calcium carbonate to give a final concentration of 0.1%, adjusted to pH 6.5, and admixed with 0.3%/g-starch of "THERMAMYL 60 L", an α-amylase commercialized by Novo Industries A/S, Copenhagen, Denmark, and then heated at 95° C. for 15 minutes. After autoclaving at 120° C. for 20 minutes, the reaction mixture was cooled to 53° C. to obtain a liquefied solution with a DE of about four. To 88 parts by weight of the liquefied starch solution, 12 parts by weight of L-ascorbic acid was added to prepare substrate solution. The substrate solution was adjusted at pH 5.0 and 53° C., admixed with 10 units/g-dextrin of the above concentrated enzyme solution having α-isomaltosyl glucosaccharide-forming enzyme activity and one unit/g-dextrin of CGTase commercialized by Hayashibara Biochemical Laboratories Inc., followed by the enzymatic reaction for 36 hours.

After inactivating enzymes by heating, the reaction mixture was adjusted to 55° C., admixed with 50 units/g-dextrin of glucoamylase, followed by the enzymatic reaction for 16 hours. After the completion of the reaction, the reaction mixture contained about 33.5%, d.s.b., of AA-2G but AA-5G and AA-6G were not detected.

The reaction mixture was heated to inactivate enzyme, and decolored and filtrated with activated charcoal. The resulting filtrate was passed through a cation exchanger (H⁺ form) column to remove minerals and successively subjected to an anion exchanger (OH⁻ form) column for allowing anions to adsorb on the resin. After washing the anion-exchanger column with water to remove D-glucose and the like, adsorbent was eluted with 0.5 N-hydrochloric acid aqueous solution. The eluate was concentrated and a concentrated solution containing about 56.1%, d.s.b., of AA-2G was obtained.

The concentrated solution was used as a material solution and subjected to column chromatography using strongly-acidic cation exchanger, according to the method described in Example 1, to collect high AA-2G content fractions. The high AA-2G content fraction, containing 96.4%, d.s.b., of AA-2G, was obtained.

The high AA-2G content fraction was concentrated under reduced pressure to give a concentration of about 77%, placed in a crystallizer, admixed with 1% to total solid basis of crystalline AA-2G as seed crystal, and adjusted to 40° C. The concentrated solution was gradually cooled to 20° C. with gentle stirring and taking two days to obtain a massecuite. Crystalline AA-2G as the first crystal was obtained in a yield of about 48%, on a material L-ascorbic acid basis, by centrifuging the massecuite using a basket-type centrifugal separator. Further, mother liquor containing about 86.7%, d.s.b., of AA-2G was collected in a yield of about 26%, on a material L-ascorbic acid basis.

The resulting mother liquor was decolored and filtrated with activated charcoal, concentrated, and subjected to column chromatography using strongly-acidic cation exchanger, according to the method described in Example 2, to collect high AA-2G content fractions.

The high AA-2G content fraction contained about 96.3%, d.s.b., of AA-2G and less than 0.1% of AA-5G and AA-6G.

Crystalline AA-2G as the second crystal was obtained in a yield of about 65%, on a dry basis of mother liquor, by concentrating the fraction, crystallizing the resulting concentrate, and separating crystal from the resulting massecuite.

The first and second crystal of AA-2G, obtained by the above method, were dried respectively, mixed and pulverized. As a result, crystalline AA-2G powder with a purity of 99% or higher was obtained in a yield of about 60%, on a dry solid basis of material L-ascorbic acid.

The product shows no reducing power and has sufficient stability and biological activity. Therefore, the product can be advantageously used for foods, anti-susceptive disease agents, cosmetics, and the like as taste-improving agent, acidifier, stabilizer, quality-improving agent, anti-oxidant substance, physiologically active substance, UV-adsorbent, material for pharmaceuticals, and chemicals as well as vitamin C reinforcement.

Example 4

According to the method described in the specification of International Patent Application No. WO 02/10361, *Bacillus globisporus* C11 (FERM BP-7144) was cultivated in a liquid culture medium consisting 4% (w/v) of "PINEDEX #4", a partial starch hydrolyzate, 1.8% (w/v) of "ASAHIMEAST", a yeast extract, 0.1% (w/v) of dipotassium phosphate, 0.06% (w/v) of sodium phosphate dodeca-hydrate, 0.05% (w/v) of magnesium sulfate hepta-hydrate, and water, for 48 hours under aeration-agitation conditions. After the completion of the culture, culture supernatant was collected as a crude enzyme preparation by centrifuging the culture at 10,000 rpm for 30 min. The resulting crude enzyme preparation was salted out with 80% ammonium sulfate solution and dialyzed. The resulting dialyzed enzyme solution was purified by ion-exchanger column chromatography using "SEPABEADS FP-DA13" gel commercialized by Mitsubishi Chemical Industries, Ltd., Tokyo, Japan; affinity column chromatography using "SEPHACRYL HR S-200" gel commercialized by Amersham Biosciences K.K., Tokyo, Japan; hydrophobic column chromatography using "Butyl-TOYOPEARL 650M" gel commercialized by Tosoh Corporation, Tokyo, Japan; and 2nd affinity column chromatography using "SEPHACRYL HR S-200" gel. Finally, a purified enzyme preparation, having about 2,000 units of the α-isomaltosyl glucosaccharide-forming enzyme activity, was obtained.

Six parts by weight of dextrin (DE of about 6) was dissolved in 30 parts by weight of water by heating. Four parts by weight of L-ascorbic acid was further added to the resulting solution under reducing condition to prepare substrate solution. The substrate solution was adjusted at pH 5.0 and 40° C., admixed with one unit/g-dextrin of the above purified enzyme preparation having α-isomaltosyl glucosaccharide-forming enzyme activity and two units/g-dextrin of CGTase commercialized by Hayashibara Biochemical Laboratories Inc., followed by the enzymatic reaction for 24 hours. After heating for inactivating enzymes, the reaction mixture was adjusted to 50° C., admixed with 50 units/g-dextrin of glucoamylase, followed by the enzymatic reaction for 16 hours. After the completion of the reaction, the reaction mixture was heated to inactivate enzyme, and decolored and filtrated with activated charcoal to obtain the filtrate.

By HPLC analysis, the resulting filtrate contains about 10.2%, d.s.b., of AA-2G but AA-5G and AA-6G were not detected.

The filtrate was passed through a cation exchanger ($H^+$ form) column to remove minerals and successively subjected to an anion-exchanger ($OH^-$ form) column for allowing anions to adsorb on the resin. After washing the column anion-exchanger column with water to remove D-glucose and the like, adsorbent was eluted with 0.5 N-hydrochloric acid aqueous solution. The eluate was concentrated and subjected to column chromatography using strongly-acidic cation exchanger to collect high AA-2G content fractions. The high AA-2G content fraction was concentrated under reduced pressure to give a concentration of about 77%, placed in a crystallizer, admixed with 2% to total solid basis of crystalline AA-2G as seed crystal, and adjusted to 40° C. The concentrated solution was gradually cooled to 20° C. taking two days to obtain a massecuite. Crystalline AA-2G with a purity of 98% or higher was obtained in a yield of about 11%, on a material L-ascorbic acid basis, by centrifuging the massecuite using a basket-type centrifugal separator.

The product shows no reducing power and has sufficient stability and biological activity. Therefore, the product can be advantageously used for foods, anti-susceptive disease agents, cosmetics, and the like as taste-improving agent, acidifier, stabilizer, quality-improving agent, anti-oxidant substance, physiologically active substance, UV-adsorbent, material for pharmaceuticals, and chemicals as well as vitamin C reinforcement.

INDUSTRIAL APPLICABILITY

As described above, the present invention relates to a process for producing AA-2G, particularly, a process for producing AA-2G, comprising a step of transferring a glucosyl residue from a glucosyl saccharide to L-ascorbic acid to form AA-2G by using α-isomaltosyl glucosaccharide-forming enzyme together with or without CGTase. By the process of the present invention, AA-5G and AA-6G, both of which are isomers of AA-2G, are not formed or formed in such a small amount that the formation of these are can not be detected in glucosyl-transfer products. Therefore, in a step of collecting AA-2G, AA-2G can be advantageously collected from glucosyl-transfer products without being affected by these isomers. By the present invention, AA-2G, a product useful in the art, can be produced in an industrial large-scale with a low cost and high yield.

The invention claimed is:

1. A process for producing 2-O-α-glucopyranosyl-L-ascorbic acid, comprising the steps of:
    allowing α-isomaltosyl glucosaccharide-forming enzyme (IMG) but not cyclomaltodextrin glucanotransferase (EC 2.4.1.19) (CGTase) to act on a solution comprising L-ascorbic acid and liquefied corn starch to obtain a reaction mixture containing 2-O-α-glucopyranosyl-L-ascorbic acid in an amount of 10% (w/w) or higher and each of 5-O-α-glucopyranosyl-L-ascorbic acid and 6-O-α-glucopyranosyl-L-ascorbic acid in an amount of less than 0.1% (w/w), on a dry solid basis; and
    collecting the 2-O-α-glucopyranosyl-L-ascorbic acid from the reaction mixture;
    wherein said α-isomaltosyl glucosaccharide-forming enzyme has an activity of forming a saccharide with a glucose polymerization degree of 3 or higher and bearing both the α-1,6 glucosidic linkage as a linkage at the non-reducing end and the α-1,4 glucosidic linkage other than the linkage at the non-reducing end from a saccharide with a glucose polymerization degree of 2 or higher and bearing the α-1,4 glucosidic linkage as a linkage at the non-reducing end by α-glucosyl-transferring reaction without increasing the reducing power of the reaction mixture; wherein said α-isomaltosyl glucosaccharide-forming enzyme is obtained from *Arthrobacter globiformis*.

2. The process of claim 1, wherein glucoamylase (EC 3.2.1.3) is allowed to act on the reaction mixture after the action of α-isomaltosyl glucosaccharide-forming enzyme on said solution.

3. The process of claim 1,
    wherein the step of collecting 2-O-α-glucopyranosyl-L-ascorbic acid comprises a step of using a strongly-acidic cation exchange resin.

4. The process of claim 1, wherein the formed 2-O-α-glucopyranosyl-L-ascorbic acid is collected in the form of a syrup, a powder, or a crystal.

5. The process of claim 3, further comprising pulverizing or crystallizing the 2-O-α-glucopyranosyl-L-ascorbic acid.

6. A process for producing 2-O-α-glucopyranosyl-L-ascorbic acid, comprising the steps of:
    allowing α-isomaltosyl glucosaccharide-forming enzyme together with cyclomaltodextrin glucanotransferase (EC 2.4.1.19) to act on a solution comprising L-ascorbic acid and liquefied corn starch to obtain a reaction mixture containing 2-O-α-glucopyranosyl-L-ascorbic acid in an amount of 10% (w/w) or higher and each of 5-O-α-glucopyranosyl-L-ascorbic acid and 6-O-α-glucopyranosyl-L-ascorbic acid in an amount of less than 0.1% (w/w), on a dry solid basis; and
    collecting the 2-O-α-glucopyranosyl-L-ascorbic acid from the reaction mixture;
    wherein said α-isomaltosyl glucosaccharide-forming enzyme has an activity of forming a saccharide with a glucose polymerization degree of 3 or higher and bearing both the α-1,6 glucosidic linkage as a linkage at the non-reducing end and the α-1,4 glucosidic linkage other than the linkage at the non-reducing end from a saccharide with a glucose polymerization degree of 2 or higher and bearing the α-1,4 glucosidic linkage as a linkage at the non-reducing end by α-glucosyl-transferring reaction without increasing the reducing power of the reaction mixture; wherein said α-isomaltosyl glucosaccharide-forming enzyme is obtained from *Arthrobacter globiformis*.

7. The process of claim 6, wherein glucoamylase (EC 3.2.1.3) is allowed to act on the reaction mixture after the action of α-isomaltosyl glucosaccharide-forming enzyme on said solution together with cyclomaltodextrin glucanotransferase.

* * * * *

SEQUENCE LISTING

<160> NUMBER OF SEQ ID NOS: 3

<210> SEQ ID NO 1
<211> LENGTH: 9
<212> TYPE: PRT
<213> ORGANISM: Arthrobacter globiformis

```
<400> SEQUENCE: 1

Tyr Val Ser Ser Leu Gly Asn Leu Ile
 1               5

<210> SEQ ID NO 2
<211> LENGTH: 9
<212> TYPE: PRT
<213> ORGANISM: Arthrobacter globiformis

<400> SEQUENCE: 2

His Val Ser Ala Leu Gly Asn Leu Leu
 1               5

<210> SEQ ID NO 3
<211> LENGTH: 13
<212> TYPE: PRT
<213> ORGANISM: Arthrobacter globiformis

<400> SEQUENCE: 3

Ala Pro Leu Gly Val Gln Arg Ala Gln Phe Gln Ser Gly
 1               5                   10
```